(12) United States Patent
Tewes et al.

(10) Patent No.: US 11,346,656 B2
(45) Date of Patent: May 31, 2022

(54) DEVICE AND METHOD FOR DETERMINING SURFACE TOPOLOGY AND ASSOCIATED COLOR

(71) Applicant: DENTSPLY SIRONA Inc., York, PA (US)

(72) Inventors: Michael Tewes, Bruhl (DE); Markus Berner, Bulach (CH)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 17/283,067

(22) PCT Filed: Jun. 3, 2019

(86) PCT No.: PCT/US2019/035160
§ 371 (c)(1),
(2) Date: Apr. 6, 2021

(87) PCT Pub. No.: WO2020/076372
PCT Pub. Date: Apr. 16, 2020

(65) Prior Publication Data
US 2021/0377509 A1 Dec. 2, 2021

Related U.S. Application Data

(63) Continuation of application No. 16/154,805, filed on Oct. 9, 2018, now Pat. No. 10,386,177.

(51) Int. Cl.
| | |
|---|---|
| *G01B 11/25* | (2006.01) |
| *A61B 5/00* | (2006.01) |
| *H04N 13/204* | (2018.01) |
| *G06T 7/90* | (2017.01) |
| *G06T 15/04* | (2011.01) |
| *A61C 9/00* | (2006.01) |
| *A61B 5/107* | (2006.01) |
| *G01B 11/24* | (2006.01) |
| *H04N 13/257* | (2018.01) |
| *H04N 13/207* | (2018.01) |

(Continued)

(52) U.S. Cl.
CPC ........ *G01B 11/2509* (2013.01); *A61B 5/0068* (2013.01); *A61B 5/0088* (2013.01); *A61B 5/1077* (2013.01); *A61B 5/4547* (2013.01); *A61C 9/006* (2013.01); *A61C 9/0066* (2013.01); *G01B 11/24* (2013.01); *G01B 11/2513* (2013.01); *G01J 3/508* (2013.01); *G06T 7/40* (2013.01); *G06T 7/90* (2017.01); *G06T 15/04* (2013.01); *G06T 17/00* (2013.01); *H04N 13/204* (2018.05); *H04N 13/207* (2018.05); *H04N 13/254* (2018.05); *H04N 13/257* (2018.05); *H04N 13/296* (2018.05); *G06T 2207/10024* (2013.01); *G06T 2215/16* (2013.01)

(58) Field of Classification Search
CPC .......................... G01B 11/2509; H04N 13/02
USPC .......................................................... 348/46
See application file for complete search history.

(56) References Cited

U.S. PATENT DOCUMENTS

2005/0225884 A1* 10/2005 Gim ...................... G02B 30/54
348/E13.013

\* cited by examiner

*Primary Examiner* — Amir Shahnami
(74) *Attorney, Agent, or Firm* — Dentsply Sirona Inc.

(57) ABSTRACT

A device and method and system for utilizing confocal measurement and an optical arrangement to produce 3D color images. A color measurement optical path and a 3D measurement optical path may coincide at least at an object side of the device, and a minimal amount of light is extracted from a monitoring beam for color measurement without affecting 3D measurement.

22 Claims, 6 Drawing Sheets

(51) Int. Cl.
*H04N 13/254* (2018.01)
*H04N 13/296* (2018.01)
*G01J 3/50* (2006.01)
*G06T 7/40* (2017.01)
*G06T 17/00* (2006.01)

DEVICE AND METHOD FOR DETERMINING SURFACE TOPOLOGY AND ASSOCIATED COLOR

CROSS-REFERENCE TO RELATED APPLICATIONS

This patent application is a National Phase application of International Application No. PCT/US2019/035160 filed Jun. 3, 2019, which claims the benefit of and priority to U.S. Pat. No. 10,386,177B1 filed on Oct. 9, 2018, which are herein incorporated by reference for all purposes.

FIELD OF THE INVENTION

The present application relates generally to a device for measuring three-dimensional (3D) and color images and, more particularly, to a color camera adapted for using a part of the optical path of a 3D camera for color measurement without disturbing 3D measurement.

BACKGROUND OF THE INVENTION

In three-dimensional measurement, the location of surface points of an object may be obtained for a plurality of applications including the measurement of the intraoral cavity. Methods for direct optical measurement of teeth and manufacture of products such as crowns and dentures, are known. Herein, digital data may be obtained and used for the computer-assisted design (CAD) or computer assisted manufacture (CAM) of tooth replacements without having to make any physical impressions of the teeth. Such methods include, for example, confocal measurement techniques such as is described in U.S. Pat. No. 6,697,164B1. Herein, a digital three-dimensional surface model that is inherently monochromatic may be provided without any color information.

In some systems, a 3D camera system for 3D and color measurement may use the same optics for color measurement as the optics for 3D measurement. In such systems, the optical paths for 3D measurement and color measurement may be configured to distribute the light onto different sensors. However light scattering and reflections due to the simultaneous usage of at least some optics for different purposes (illumination, detection, etc.) may occur, effectively reducing image quality of the color images.

U.S. patent application Ser. No. 16/003,592 and U.S. patent application Ser. No. 16/003,628 disclose devices, methods and systems for generating dynamic projection patterns in a camera for 3D measurement. They are hereby incorporated by reference in their entirety for background disclosure purposes.

U.S. Pat. No. 3,681,519A discloses a handheld dental camera for carrying out optical 3D measurement comprising a light source, achromatic objective and a color sensor wherein the light source may be configured to emit a beam that may be focused onto the surface of an object by means of the chromatic objective. The beam may then be reflected by the surface and the reflected beam may be capable of being detected by the color sensor for measurement.

U.S. Pat. No. 7,787,132B2 describes a chromatic confocal method and apparatus for the rapid three-dimensional measurement of an object using an array of polychromatic point light sources, a planar detector matrix, a beam splitter for lateral spectral separation, and an objective for illuminating and recording the object. Spectral defined reference light bundles may be generated, injected into a detection beam path through a reference beam path and, following spectral splitting, focused on the detector matrix as reference image points, wherein laterally shifted sub-matrices may be numerically defined on the detector matrix for spectral analysis of the object light, which sub-matrices may be implemented as spectral cells for three-dimensional measurement of the shape of the object U.S. patent application Ser. No. 14/268,201 illustrates a method of performing a three-dimensional scan of an object including applying an optical contrast powder to the object and illuminating the object with light. A first and a second two-dimensional (2D) color image data corresponding to the object are generated and a first and a second 2D monochrome image data corresponding to the object may be generated using the first and second 2D color image data. 3D data corresponding to the object may then be generated using the first and second monochrome 2D image data and color 3D image data corresponding to the object may be generated by adding color information to the 3D data.

U.S. patent application Ser. No. 10,007,715 shows a method and an apparatus for acquiring surface topography wherein the surface being acquired may be illuminated by illumination sources with patterns of light from an optical perspective and the light reflected off the surface may be captured by image sensors from an optical perspective that may be different from the perspective of the illumination. The images obtained may be of the surface with one or more patterns superimposed upon the surface. The surface topography may be computed with a processor based upon the patterned image data, a known separation between the illumination sources and the imaging sensors, and knowledge about how the patterns of light are projected from the illumination sources. US2017374350A1 discloses an optical system in a 3D focus scanner. US2015037750A1 discloses methods and systems for generating color images. US2010311005A1 discloses an apparatus for dental surface shape and shade imaging.

SUMMARY OF THE INVENTION

Existing limitations associated with the foregoing, as well as other limitations, may be overcome by a device and method for utilizing confocal measurement and an optical arrangement to produce color images of at least a portion of an object, said optical arrangement including an extraction/deflecting mirror disposed in a color measurement optical path for extracting a "small" amount of light for color measurement, said small amount of light being extracted from light in a 3D measurement optical path such that 3D measurement may not be affected or substantially affected by the color measurement and such that contributions to the color images by internal reflections may be minimized. "Color measurement" may be used hereinafter to refer to taking colored images and/or a colored live view of an object. The color measurement optical path and the 3D measurement optical path may coincide at least at an object side of the device, and in order to extract the small amount of light without substantially affecting 3D measurement, the device may be constructed to have a large depth of field for the color measurement and the extraction mirror may be configured to have a size smaller than (e.g. less than 20%) of the diameter of a beam used for 3D measurement as explained hereinafter. By the positioning of the extraction mirror on the color measurement optical path, instead of, for example, using full area extraction with beam splitters, only the reflected beams which contribute lowest to the depth/3D information of the object 10 during 3D measurement, may be disturbed (removed from the 3D optical path and used for color measurement).

According to an aspect of the present invention a device may be provided for determining the surface topology and associated color of an object, comprising: a 3D measurement optical path; a color measurement optical path configured to have a depth of field about as large (i.e. equal to or smaller than, e.g. about 75% of the 3D measurement range) a 3D-measurement range of the camera; an extraction mirror disposed within the color measurement optical path and configured to extract a first portion of the monitoring beam; a light source for providing an illumination beam for illuminating the object; a variable imaging optics arranged within the device to focus the illumination beam onto the object and adaptable to change a position of a focal plane of the device, so that features of the illumination beam are projected onto the object with maximum contrast at the focal plane, the illumination beam being reflected from the object as a monitoring beam; wherein the color measurement optical path has a color image sensor disposed therein, the color image sensor adapted to detect the first portion of the monitoring beam to form color images, wherein the 3D measurement optical path has a 3D image sensor disposed therein, the 3D image sensor is adapted to detect a second portion of the monitoring beam to form 3D images.

According to another aspect of the present invention the device may be provided including one or more combinations of the following: (i) wherein the light source is polarized in a first polarization direction, (ii) further comprising a polarization filter disposed within said color measurement optical path, which polarizes the light in the color measurement optical path in a second polarization direction perpendicular to the first polarization direction, to block internal reflections from reaching said color image sensor, (iii) wherein the color measurement optical path and the 3D measurement optical path coincide at least at an object side of the device, (iv) further including a color aperture stop in the relay optic that lies in the conjugate plane of the extraction mirror, (v) wherein the color aperture stop has a numerical aperture configured such that a large depth of field of the color measurement optical path (about as large as a 3D-measurement range of the camera) is obtained, (vi) further including a signal processing unit for mapping the color images to a 3D model, (vii) further including a display for displaying 3D color representations of the object. (viii) wherein the light source is configured to project white light for color measurement, (ix) wherein the light source is configured to project blue light for 3D measurement.

In another aspect herein, a device may be provided for determining the surface topology and associated color of an object, comprising: scanning means adapted for providing depth data of the object for 3D measurement; imaging means adapted for providing color image data of said object associated with said depth data for color measurement; wherein the imaging means is adapted with an extraction mirror for extracting a portion of a monitoring beam reflected from the object, wherein the imaging means has a depth of field configured to be about as large as the 3D-measurement range of the camera such that said portion of the monitoring beam comprises rays that contribute the least to the 3D information of the object such that 3D measurement is not disturbed or substantially disturbed.

In yet another aspect of the present invention, a method for determining the surface topology and associated color of an object may be provided comprising: providing a 3D measurement optical path and a color measurement optical path such that a depth of field of the color measurement optical path is configured to be about as large as a 3D-measurement range of the camera; controlling a light source of a device to generate an illumination beam for illuminating the object for color measurement and for 3D measurement, controlling a variable imaging optics of the device to focus the illumination beam onto the object and to change a position of a focal plane of the device so that features of the illumination beam are projected onto the object with maximum contrast at the focal plane, obtaining a monitoring beam from a reflection of the illumination beam from the object, extracting a first portion of the monitoring beam for color measurement of said object such that said first portion comprises rays that contribute the least to the 3D information of the object such that 3D measurement is not disturbed or substantially disturbed.

In another aspect of the present invention, the method may be provided including one or more combinations of the following; (i) further comprising mapping the color images to a 3D model formed from the 3D images (ii) further comprising polarizing the light source with a first polarization direction, (iii) further comprising blocking or substantially blocking internal reflections in the device from reaching a color image sensor by providing an illumination beam which is polarized in a first polarization direction and a polarization filter disposed within said color measurement optical path, wherein the light in the color measurement optical path is polarized in a second polarization direction perpendicular to the first polarization direction, such that about 50% of the extracted monitoring beam is allowed to pass through, (iv) further comprising forming an intermediate color image in a plane of the device, (v) further comprising imaging the intermediate color image onto a color image sensor through a color aperture stop by a relay optics, (vi) wherein the light source is controlled such that when the focal plane is outside a 3D measurement range of the camera, said range being the z-range of the 3D volume, a color measurement light is switched on and one or more images are taken for color measurement in a first predetermined duration of time, (vii)
wherein the color measurement light is white light, (viii) wherein the light source is controlled such that when the focal plane is inside a 3D measurement range for the camera, a 3D measurement light is switched on and one or more images are taken for 3D measurement in a second predetermined duration of time, (ix) wherein the 3D measurement light is blue light.

In yet another aspect of the present invention, a system for determining the surface topology and associated color of an object may be provided, comprising: at least one processor operable to: control a light source of a device to generate an illumination beam for illuminating the object for color measurement and for 3D measurement, control a variable imaging optics of the device to focus the illumination beam onto the object and to change a position of a focal plane of the device, obtain a monitoring beam from a reflection of the illumination beam from the object, extract a first portion of the monitoring beam for color measurement of said object such that said first portion comprises rays that contribute the least to the 3D information of the object such that 3D measurement is disturbed or substantially disturbed.

The device, method and system may be useful for reducing the noise generated in color images compared to other devices/techniques and may result in better data quality and/or higher Z-resolution in 3D images than compared to other devices/techniques.

Further features and advantages, as well as the structure and operation of various embodiments herein, are described in detail below with reference to the accompanying drawings.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Different ones of the Figures may have at least some reference numerals that may be the same in order to identify the same components, although a detailed description of each such component may not be provided below with respect to each Figure.

DETAILED DESCRIPTION OF THE INVENTION

Device for 3D Color measurement

Figure 1:
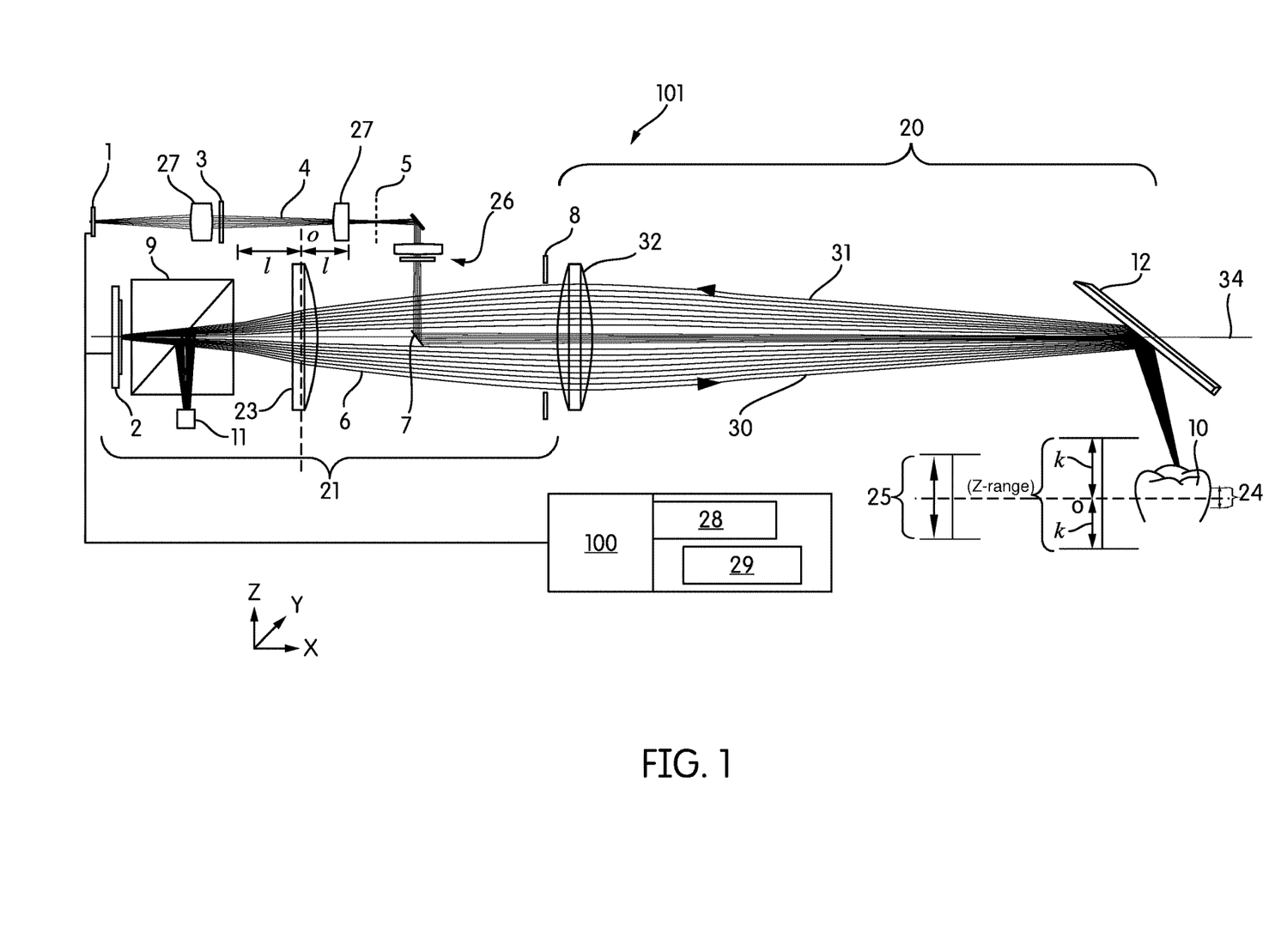
FIG. 1 is a block diagram of a device illustrating an exemplary embodiment of the present invention.
Figure 2:
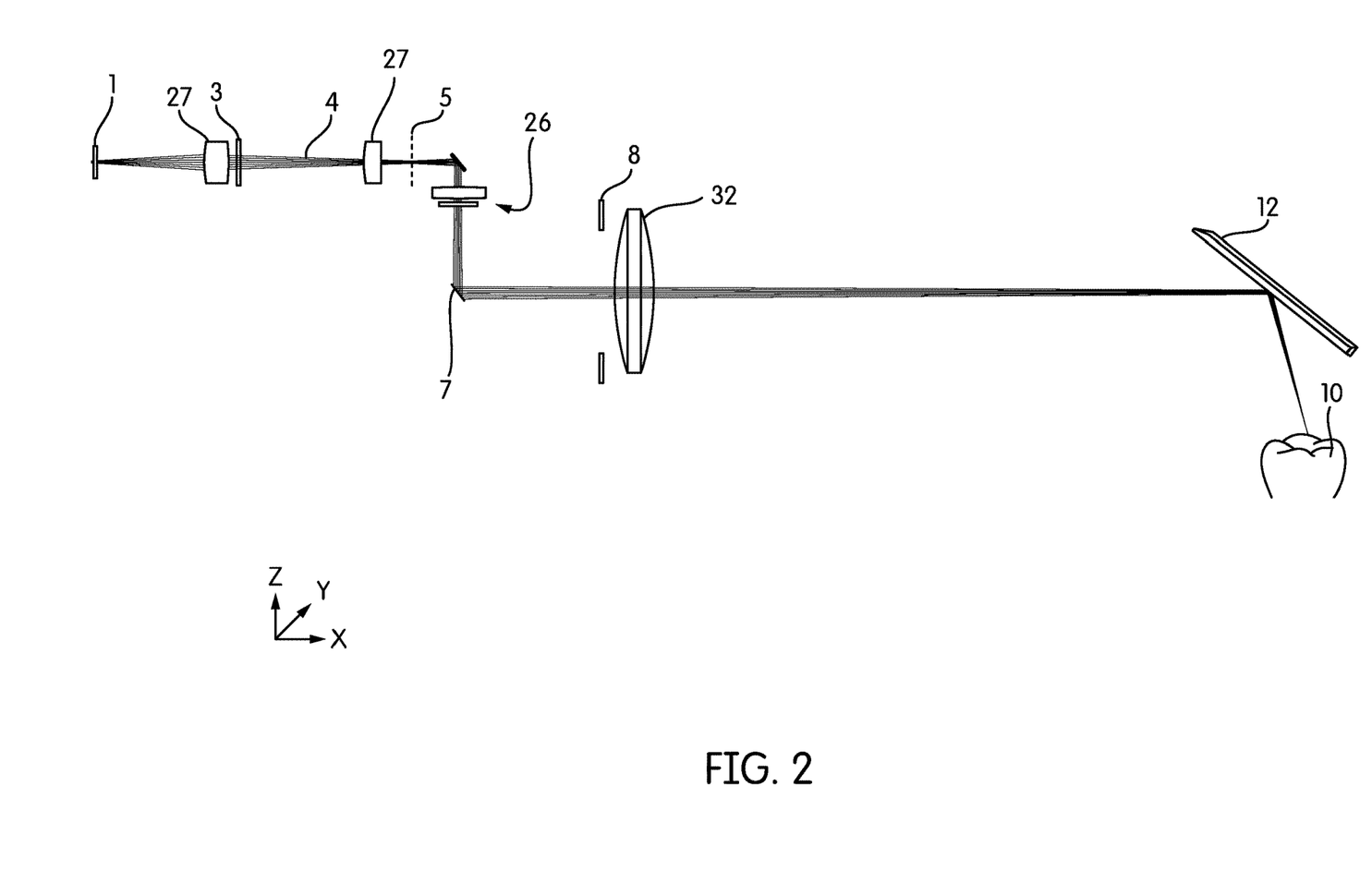
FIG. 2 illustrates a part of the block diagram of FIG. 1 showing an optical path for color measurement.

In accordance with example aspects described herein, a device 101 for utilizing confocal measurement and an optical arrangement for 3D color measurement may be realized. The device 101 may include a 3D camera system and a color camera system. The device 101 may also use said confocal measurement and optical arrangement to produce 3D color images (surface topology and corresponding color/colors of said surface) of an object 10 or of at least a portion of the object. The optical arrangement may include an extraction mirror 7 disposed in a color measurement optical path 4 (shown in FIG. 2) for extracting a minimal amount of light for color measurement by the color camera, said minimal amount of light being extracted from light from a 3D measurement optical path 6 (shown in FIG. 3) such that 3D measurement using the 3D camera may not be affected or substantially affected by the color measurement and such that internal reflections may be minimized. Herein, (i) the color camera and the 3D camera may share optics at least at an object side 20 of the device (ii) the color measurement optical path 4 and the 3D measurement optical path 6 may coincide at least at said object side 20 of the device, and (iii) in order to extract the minimal amount of light from a monitoring beam 31 without affecting 3D measurement, the device 101 may be constructed to have a depth of field 25 for the color measurement and/or a relatively small depth of focus 24 for the 3D measurement as explained hereinafter. The depth of focus 24 may be, for example, about 1/100 of the depth of field 25. In order to obtain said "minimal" amount of light, the extraction mirror 7 may be configured to have a size smaller than (e.g. less than 50% or, less than 40%, preferably less than 30%, more preferably less than 20%, and even more preferably less than 10%, but still being larger than 0%) of the diameter of a 3D measurement optical path 6. A minimal amount of light may comprise less than 25% (e.g. less than 16%, preferably less than 9%, more preferably less than 4%, and even more preferably less than 1%), but more than 0% of the monitoring beam or of part of the monitoring beam used for 3D measurement. The extraction mirror 7 may similarly be smaller than (e.g. less than 20%), but larger than (e.g., greater than 0%) of a diameter of the aperture stop 8.

In an embodiment of the present invention, a depth of field 25 for the color measurement may be about 15 mm (+/−20%). A 3D measurement range for the camera may be about 20 mm (+/−20%), a depth of focus 24 for 3D measurement may be about 0.5 mm (+/−20%) and a diameter of the extraction mirror 7 may be about 2 mm (+/−20%).

In confocal measurements, light such as projected light patterns may be used to generate optical features on the surface of an object 10 to be measured and optical 3D measuring methods which operate according to confocal/depth of focus principles may be used to measure the object 10. Herein light (e.g. a temporal varying light or static pattern) from a light source 11, such as an LED source with a microlens array, may be projected through a beam splitter cube 9 onto an imaging optics 23 and through system aperture stop 8 and lens 32 onto the object 10. The light may subsequently be reflected by the object 10 to be imaged onto the 3D sensor 2. The beam splitter cube 9 may separate outgoing beams of the light source 11 from incoming monitoring beams 31 of object 10. For 3D measurement, the variable imaging optics 23 may have a depth of focus 24 that may be much smaller than the thickness of the object 10 such that it may be used in the confocal 3D measurement for projection and detection. The variable imaging optics 23 may be a movable imaging optics, liquid lenses, flexible lenses or the like. Thus the temporal varying light pattern may be imaged sharply (or with maximum contrast) on the 3D sensor 2, only for regions of the object 10 that intersect with the depth of focus 24 of the variable imaging optics 23. By the use of the variable imaging optics 23, the focal plane of the variable imaging optics 23 may be moved through the volume of the object 10. The focal plane of the color camera may not be affected as the variable imaging optics 23 is not in the color measurement optical path 4. In off-focus regions the light blurs and creates a constant average intensity that distinguishes the off-focus regions from the focused regions. Only the focused regions/sharply imaged regions of the object may therefore create a modulated signal for the 3D sensor 2. By using various structured illumination patterns, confocal measurement/depth of focus principles, along with noise reduction and data density increasing setups/techniques, 3D surface profiles of objects may be measured. Moreover, by modulating with a predetermined frequency, only signals corresponding to that frequency may be detected for further processing.

However the images captured by the 3D-sensor 2 may not contain color information. Therefore a separate color image sensor 1 may be used to detect color information of the object 10. 3D color cameras may use the same optics simultaneously for illumination and detection. Light scattering from walls and internal reflections (such as reflections due to the air/glass interface of lens 32 which may be, for example, about 0.05-4 percent of the illumination beam 30 and reflections from edges of the extraction mirror 7) may therefore occur inside the cameras as a result and produce unwanted effects in any color images taken. In an embodiment according to the present invention, the effects of the light scattering/internal reflections (such as for example, a reduction of dynamic range and/or a constant background image on the color image sensor 1) may be reduced and/or eliminated using an extraction mirror 7 and a polarizer/polarization filter 26 behind system aperture stop 8. The extraction mirror may be used to extract a portion of light reflected from the object 10 to detect a color of the object 10. The extracted light may then be passed through the polarizer/polarization filter 26 to block out light with a same polarization as a polarization of the illuminating beam 30. Generally, a polarization direction of light may be altered by scattering/reflection, so that only part of the scattered (reflected) light maintains its original polarization.

In an embodiment of the present invention, the illumination beam 30 may first be polarized in a first polarization direction and the polarizer/polarization filter 26 may be configured such that (i) polarization maintaining internally reflected light (in the first polarization direction) such as a portion of reflections caused by the surface of lens 32 may be prevented from passing through the polarizer/polarization filter 26 (e.g. at least to a predetermined extent) and (ii) part of the monitoring beam 31 which may become unpolarized or substantially unpolarized due to having been reflected by object 10 or changed polarization by passing a lambda quarter plate may be allowed to pass through the polarization filter 26 after being extracted by the extraction mirror 7 (i.e. the unpolarized monitoring beam 31 may be polarized in a second polarization direction by the polarizer/polarization filter 26 said second polarization direction being perpendicular to the first polarization direction such that about 50% of the extracted monitoring beam 31 is allowed to pass through the polarization filter 26). However, internal reflections/scattered light from the internal walls of the camera may also be substantially unpolarized. Therefore the unpolarized internal reflections may not be fully blocked by the polarization filter 26. However since said unpolarized internal reflections may mostly originate from a point outside of a center of the extraction mirror 7, said unpolarized internal reflections may be substantially blocked at the color aperture stop 3, due the aperture of the color aperture stop 3 being configured to be smaller than an image of the extraction mirror 7. As a result only the light from the center of the extraction mirror 7 may be allowed to pass through the color aperture stop 3.

An intermediate color image may be formed in the plane 5. This intermediate color image may be imaged through color aperture stop 3 by the relay optics 27 onto the color image sensor 1 for color measurement.

The device 101 may further include a computer system 100 for generating and displaying 3D color representations of the object 10. The computer system 100 may comprise a signal preprocessing or processing unit 28 and an acquisition unit 29 and may be electrically connected to and/or in communication with the color image sensor 1, the 3D sensor 2, the light source 11 and the variable imaging optics 23.

In an embodiment herein, during the exposure/scan of object 10, the signal preprocessing unit 28 may collect the single image frames of the color image sensor 1 and the 3D sensor 2. It may then map the color data of color image sensor 1 with the 3D model created from the 3D data of 3D sensor 2.

Method for 3D Color measurement

Figure 4:
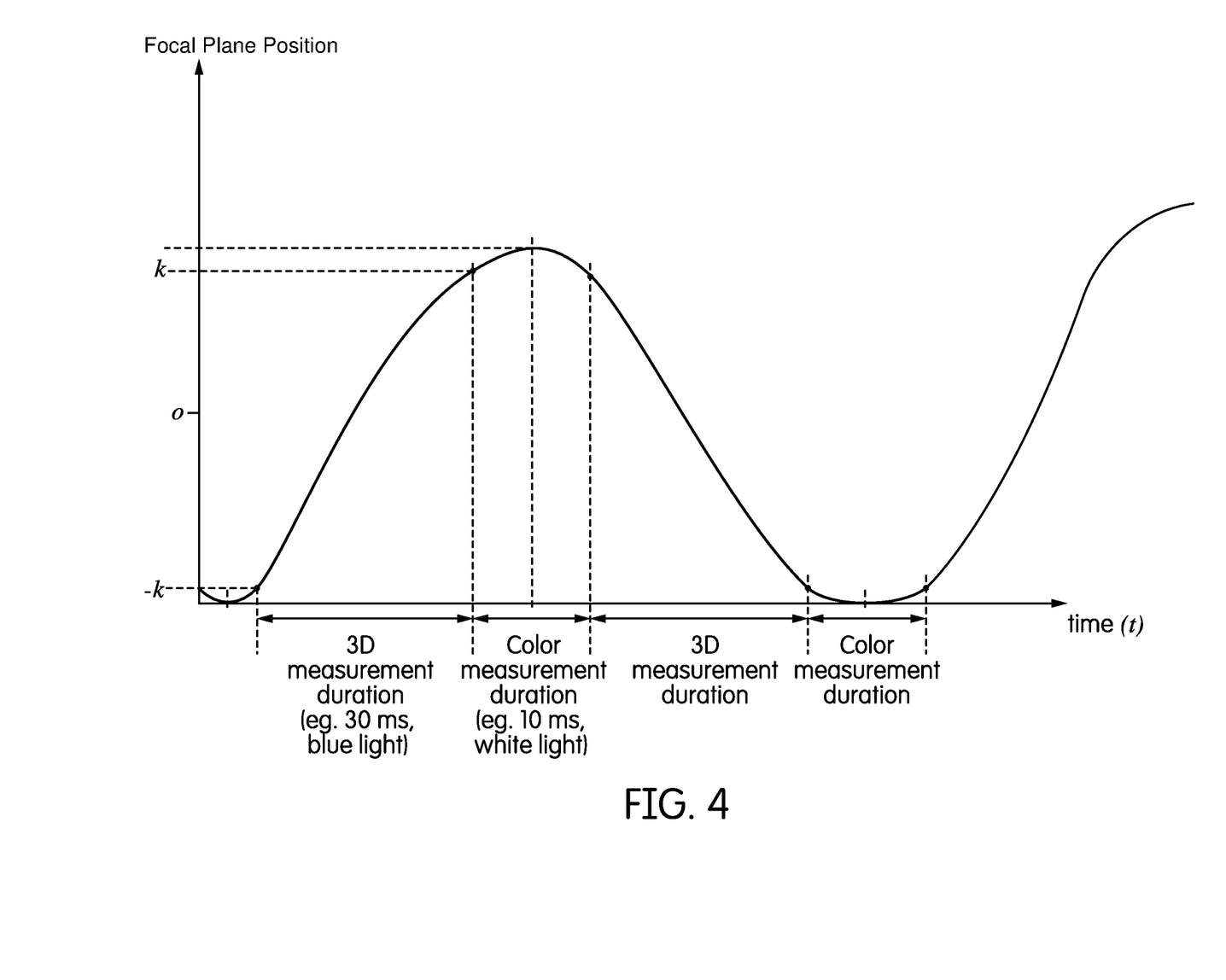
FIG. 4 is a graph showing a relationship between a position of a focal plane of the movable imaging optics and time according to an exemplary embodiment of the present invention.
Figure 5:
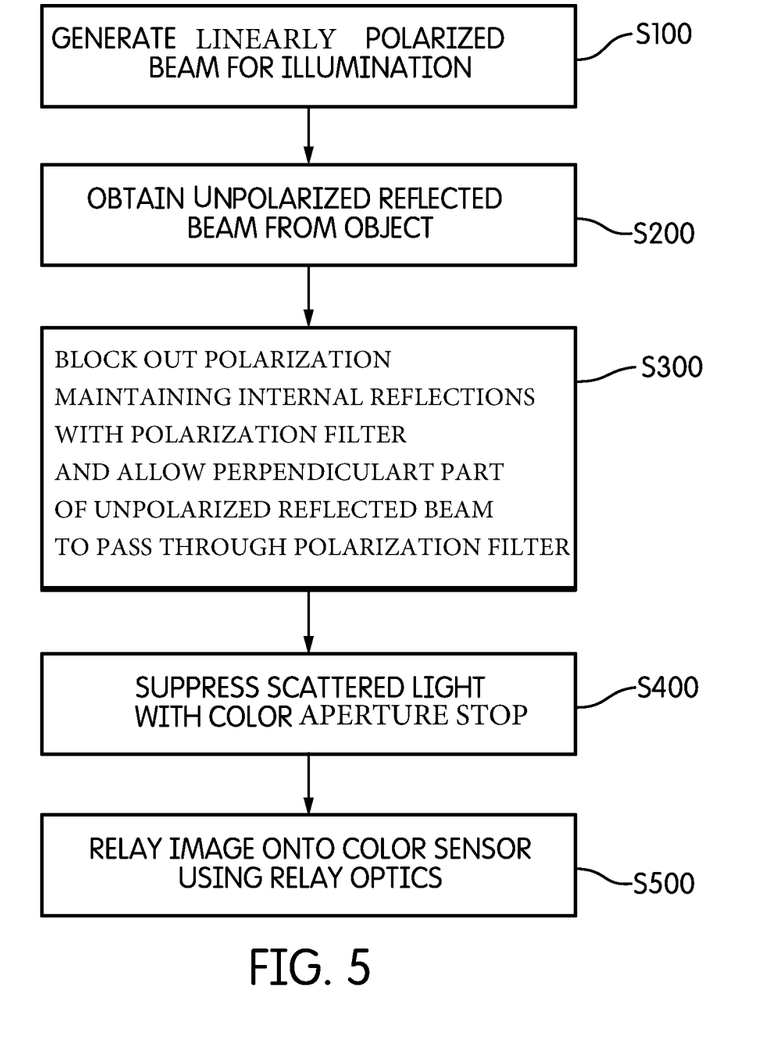
FIG. 5 is a flow chart showing a method according to an exemplary embodiment of the present invention.

Having described components of the device 101 of FIG. 1, a method of operating the device 100 will now be further described in conjunction with FIGS. 4 and 5 which show a method for 3D color measurement.

Turning now to FIG. 5, an illumination beam of light 30 may be generated by control of the light source 11 to illuminate object 10 as shown in Step S100. The illumination beam 30 may preferably be a polarized beam of light. A focal plane of the variable imaging optics 23 may be controlled for color measurement and for 3D measurement as described hereinafter.

In an exemplary embodiment according to the present invention, a small depth of focus 24 may be used for 3D measurement and a larger depth of field 25 may be used for color measurement. 3D measurement may occur by moving the focal plane of the variable imaging optics 23 through the volume of the object 10. In off-focus regions of the object 10 the illumination beam 30 blurs and may create a constant average intensity that distinguishes the off-focus regions from the focused regions. In the focused regions the object 10 may create a modulated signal for the 3D sensor 2 to measure. Since a large depth of field 25 may be used for color measurement, color images may be taken at said off focus regions, wherein a signal may be created for the color measurement.

In an exemplary embodiment according to the present invention, white light may be used for the color measurement and blue light may be used for 3D measurement. In another exemplary embodiment, any color may be used for 3D-measurment and white light or a sequential illumination with different colors (e.g. red, green, blue), which sum up to white may be used. Herein the light source 11 may be switched between the color measurement light and the 3D measurement light. FIG. 4 in conjunction with FIG. 1 shows a relationship between the position of a focal plane of the movable imaging optics and time. The variable imaging optics 23 may be controlled such that when the focal place is outside a 3D measurement range (−k to k), white light may be switched on at the light source 11 and one or more images may be taken for color measurement. In an exemplary embodiment of the present invention, the depth of focus 24 may move as the focal plane of the 3D optics is moved by the variable imaging optics 23. However the depth of field 25 may remain constant during such movement. Herein, when the focal plane is outside the 3D measurement range (outside the range −k to k), structured light from the light source 11 may be focused outside the 3D measurement range and may not be focused inside the 3D measurement range. Since the depth of field 25 may be inside said 3D measurement range, color images of the tooth may be taken such that the structured illumination may not be seen in said color images. In an embodiment, the color images may be taken within a predetermined duration (e.g. one or more images within a 10 ms interval). Likewise the variable imaging optics may be controlled such that when the focal plane is inside a 3D-measurement range (−k to k) used for 3D measurement, blue light may be switched on at the source 11 and one or more images may be taken for 3D measurement. Herein, the structured illumination used for 3D measurement is seen in the 3D images. In an embodiment herein, 3D images may be taken within a predetermined duration (e.g. one or more images within a predetermined time interval, e.g. 80 images, within a 30 ms interval).

Figure 3:
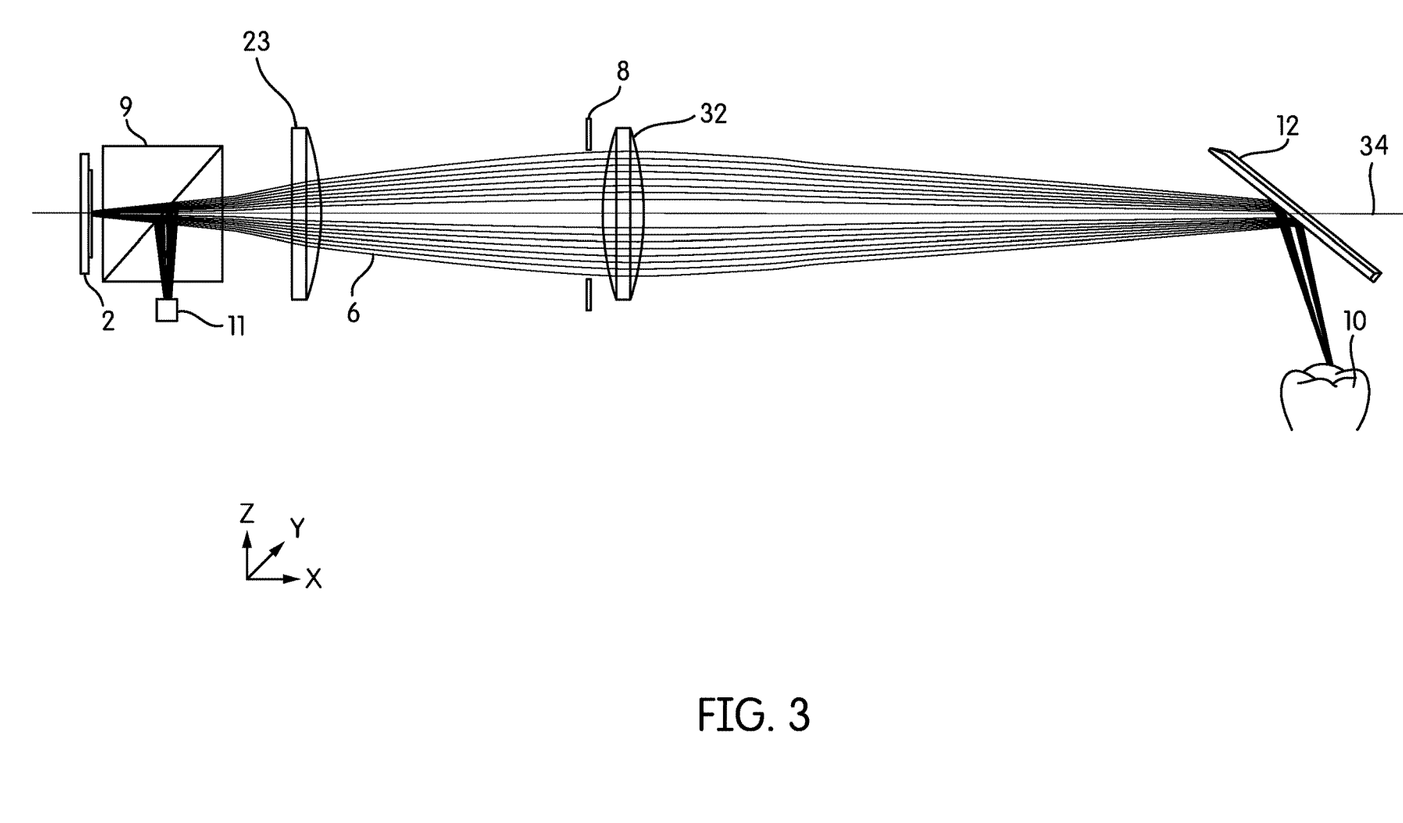
FIG. 3 illustrates a part of the block diagram of FIG. 1 showing an optical path for 3D measurement according to an exemplary embodiment of the present invention.

In another embodiment herein, an electronic shutter (not shown) of the 3D sensor may be closed during color image acquisition. Likewise, an electronic shutter of the color image sensor may be closed during 3D image acquisition During illumination of the object 10, the illumination beam 30 may be projected though system aperture stop 8 and deflected onto object 10 by a mirror 12. Upon receiving the illuminating beam 30, the object 10 may reflect the illumination beam 30 into a monitoring beam 31, said monitoring beam 31 being projected through the system aperture stop 8 into a sensor side 21 of the device 101, Step S200. At the sensor side 21, the extraction mirror 7 may deflect a portion of the monitoring beam towards a polarizing filter 26 for color measurement, said portion corresponding to the color measurement optical path 4. Contrary to a small depth of focus 24 being used for 3D measurement, the color measurement may use a larger depth of field 25. A small numerical aperture (diameter) of color aperture stop 3 may be used to achieve the large depth of field 25. The extraction mirror may lie in a conjugate plane of the color aperture stop 3 therefore its size may be proportional to the color aperture stop diameter in the color optics. The use of a small color aperture stop diameter may thus enable a small extraction mirror 7. Using the small extraction mirror 7 only a small amount of light may be extracted from the 3D measurement optical path 6. By using the extraction mirror 7 instead of for example providing a full area extraction using beam splitters, only the beams of the 3D measurement optics, which contribute lowest to the depth information of the object point, may be disturbed. As shown in FIG. 1, the positioning of the extraction mirror 7 may block central rays of the monitoring beam 31 during 3D measurement but this may result in some acceptable imaging artefacts as the numerical aperture may not be affected and therefore the z-resolution may stay the same. Therefore it may be preferable to place the extraction mirror near the center of the optical axis 34 as shown in FIG. 1 and FIG. 3 rather than away from the optical axis 34.

The polarizing filter 26 may block out internal reflections while allowing the monitoring beam 31 to pass through as shown in Step S300. Herein, the polarization filter 26 block out polarization maintaining internal reflections and allow a perpendicular part of the unpolarized or substantially unpolarized extracted monitoring beam 31 to pass through the polarization filter 26. As shown in Step S400, color aperture stop 3 may suppress internal reflections that are scattered internally and that would otherwise be propagated onto the color image sensor 1. An intermediate color image formed in the image plane 5 may be imaged through the color aperture stop 3 onto the color image sensor 1 by relay optics 27 as shown in Step S500.

After obtaining a preferably predetermined number of 3D images and color images, they may be mapped together wherein, for example, the color images may be mapped to a 3D model formed from the 3D images. Herein, from a camera calibration, there may be a knowledge of what every 3D point corresponds to in a 2D-color-image (i.e. a 3D to 2D mapping). This map may be used to find for every 3D data point in the 3D model, a corresponding pixel in the 2D-color-image. The color of this pixel may then be assigned to the data point and can thus be displayed in a 3D-view of the measured model.

Computer System for 3D Color Measurement

Having described a device 101 for 3D color measurement, reference will now be made to FIG. 6, which shows a block diagram of a computer system 100 that may be employed in accordance with at least some of the example embodiments herein. In an embodiment herein the computer system 100 may form a part of the device 101. In another embodiment herein, the computer system may be separate from the device 101. Although various embodiments may be described herein in terms of this exemplary computer system 100, after reading this description, it may become apparent to a person skilled in the relevant art(s) how to implement the disclosure using other computer systems and/or architectures.

The computer system 100 may include at least one computer processor 122. The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, a cross-over bar device, or a network). In an embodiment herein, the processor 122 includes a CPU that obtains an image stack from the signal preprocessing unit 28 of the device 101 h. The stack may be temporarily stored in memory and then analyzed. Color image data may be mapped to 3D model by the processor 122. Upon moving the device 101 while recording, a series of point clouds may be formed. The CPU 123 may rotate and translate the point clouds to give a consistent 3D-model for rendering on the display interface 126 of the computer system 100. In another embodiment, the CPU may match image features detected by the sensor 4 to the projected features and convert them to a 3D-point cloud by triangulation with each image resulting in a separate point cloud. Herein, the sensor may optionally not possess in-pixel demodulating functionality. When the camera is moved a series of point clouds results. These point clouds may be rotated and translated individually by the CPU 123 to give a consistent 3D-model. This 3D-model may be finally rendered on the display 128. In embodiment herein, the signal preprocessing unit 28 of may be incorporated into the device 101 and in another embodiment herein, the signal preprocessing unit 28 may be outside the device 101.

The display interface (or other output interface) 126 may forward video graphics, text, and other data from the communication infrastructure 124 (or from a frame buffer (not shown)) for display on a display unit 128 (which, in one example embodiment, may form or be included in the display unit 128 of FIG. 1). For example, the display interface 126 may include a video card with a graphics processing unit.

The computer system 100 may also include an input unit 130 that may be used by a user of the computer system 100 to send information to the computer processor 122. The input unit 130 may include a trackball or other input device such as a keyboard and/or touchscreen monitor. In one example, the display unit 128, the input unit 130, and the computer processor 122 may collectively form a user interface.

One or more steps of generating the controlling the device 101 to generate 3D color images may be stored on a non-transitory storage device in the form of computer-readable program instructions. To execute a procedure, the processor 122 loads the appropriate instructions, as stored on storage device, into memory and then executes the loaded instructions.

Figure 6:
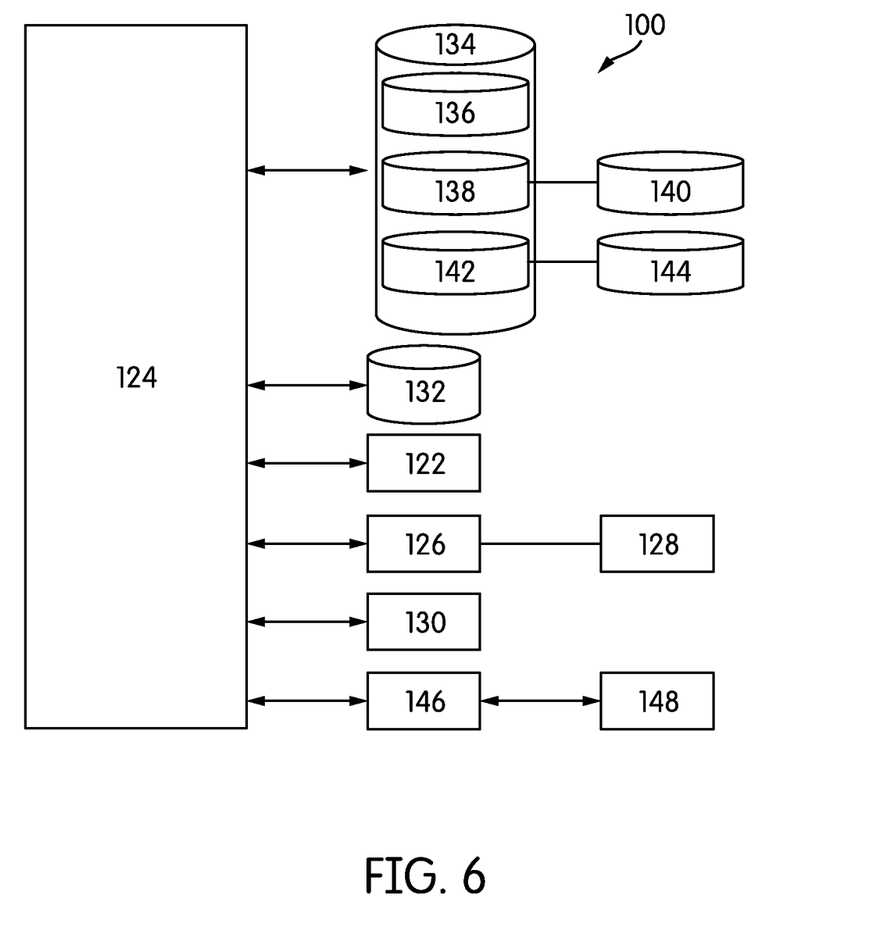
FIG. 6 illustrates a computer system according to an exemplary embodiment of the present invention.

The computer system 100 of FIG. 6 may comprise a main memory 132, which may be a random access memory ("RAM"), and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCM-CIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods described. Accordingly, the computer programs may control the computer system 100 and other components of the device 101.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, may cause the computer system 100, and more generally the device 101 in some embodiments, to perform all or some of the methods described herein.

Lastly, in another example embodiment hardware components such as ASICs, FPGAs, and the like, may be used to carry out the functionality described herein. Implementation of such a hardware arrangement so as to perform the functions described herein will be apparent to persons skilled in the relevant art(s) in view of this description.

In view of the foregoing description, it may be appreciated that the example embodiments described herein provide a device, method for generating 3D color images in a camera, for example, a dental camera.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

What is claimed is:

1. A device for determining the surface topology and associated color of an object, comprising:
a 3D measurement optical path including a light source, a variable imaging optics, and a lens that are arranged to define a depth of focus;
a color measurement optical path including a color image sensor and an optical assembly that are arranged to define a depth of field,
wherein the depth of field is larger a depth of focus,
wherein the light source is adapted to provide a structured illumination beam for illuminating the object,
wherein the variable imaging optics is arranged to focus the structured illumination beam onto the object and adapted to move a position of a focal plane of through the volume of the object;
an extraction mirror disposed within the color measurement optical path and configured to extract a first portion of a monitoring beam coming from the object,
wherein the color image sensor is adapted to detect the first portion of the monitoring beam to form color images,
wherein the 3D measurement optical path has a 3D image sensor disposed therein, the 3D image sensor is adapted to detect a second portion of the monitoring beam to form 3D images,
wherein the depth of field is equal to or smaller than the 3D measurement range of the 3D image sensor,
wherein the color images of the object are taken such that the structured illumination is not seen in said color images,
wherein the light source is controlled such that when the focal plane is outside the 3D measurement range, a light for color measurement is switched on and one or more images are taken for color measurement in a first predetermined duration of time,
wherein the light source is controlled such that when the focal plane is inside the 3D measurement range, a light for 3D measurement is switched on and one or more images are taken for 3D measurement in a second predetermined duration of time.

2. The device according to claim 1, wherein said extracted first portion of the monitoring beam comprises less than 25% of rays of the monitoring beam and more than 0% of rays of the monitoring beam.

3. The device according to claim 2, wherein said extracted first portion of the monitoring beam comprises less than 2% of rays of the monitoring beam and more than 0% of rays of the monitoring beam.

4. The device according to claim 1, wherein the extraction mirror is disposed on the optical axis of the 3D measurement optical path.

5. The device according to claim 1, wherein the illumination beam is polarized in a first polarization direction.

6. The device according to claim 5, further comprising a polarization filter disposed within said color measurement optical path, configured to polarize the light in the color measurement optical path in a second polarization direction perpendicular to the first polarization direction, to block internal reflections from reaching said color image sensor, and to allow the first portion of the monitoring beam to pass through.

7. The device according to claim 1, wherein the color measurement optical path and the 3D measurement optical path coincide at least at an object side.

8. The device according to claim 1, wherein the optical assembly includes a color aperture stop in a relay optic that lies in a conjugate plane of the extraction mirror, said color aperture stop configured to provide said depth of field of the color measurement optical path.

9. The device according to claim 1, further including a signal processing unit for mapping the color images to a 3D model formed from the 3D images.

10. The device according to claim 1, further including a display for displaying 3D color representations of the object.

11. The device of claim 1, wherein the light source is configured to project white light for color measurement.

12. The device of claim 1, wherein the light source is configured to project blue light for 3D measurement.

13. A method for determining the surface topology and associated color of an object, comprising:
    providing a 3D measurement optical path including a light source, a variable imaging optics, and a lens that are arranged to define a depth of focus; and
    a color measurement optical path including a color image sensor and an optical assembly that are arranged to define a depth of field,
    wherein the depth of field is larger than the depth of focus;
    controlling the light source to generate a structured illumination beam for illuminating the object for color measurement and for 3D measurement,
    controlling the variable imaging optics to focus the illumination beam onto the object and to change a position of a focal plane through the volume of the object;
    obtaining the monitoring beam from a reflection of the illumination beam from the object;
    providing an extraction mirror disposed within the color measurement optical path to extract a first portion of the monitoring beam;
    detecting the first portion of the monitoring beam for color measurement of said object to form color images, and
    detecting a second portion of the monitoring beam for 3D measurement of said object to form 3D images, characterized in that the depth of field is equal to or smaller than the 3D measurement range of the 3D image sensor, whereby the color images of the object can be taken such that the structured illumination is not seen in said color images,
    controlling the light source such that when the focal plane is outside the 3D measurement range, the light for color measurement is switched on and one or more images are taken for color measurement in a first predetermined duration of time,
    controlling the light source such that when the focal plane is inside the 3D measurement range, the light for 3D measurement is switched on and one or more images are taken for 3D measurement in a second predetermined duration of time.

14. The method according to claim 13, wherein said extracted first portion of the monitoring beam comprises less than 25% of rays of the monitoring beam and more than 0% of rays of the monitoring beam.

15. The method according to claim 14, wherein said extracted first portion of the monitoring beam comprises less than 2% of rays of the monitoring beam and more than 0% of rays of the monitoring beam.

16. The method according to claim 13 further comprising mapping the color images to a 3D model formed from the 3D images.

17. The method according to claim 13, further comprising polarizing the illumination beam with a first polarization direction.

18. The method according to claim 17, further comprising blocking or substantially blocking internal reflections from reaching a color image sensor and allowing the first portion of the monitoring beam to pass through by providing a polarization filter disposed within said color measurement optical path, which polarizes the light in the color measurement optical path in a second polarization direction perpendicular to the first polarization direction.

19. The method according to claim 13, further comprising forming an intermediate color image in a plane of the device.

20. The method according to claim 19, further comprising imaging the intermediate color image onto a color image sensor through a color aperture stop by a relay optics in the optical assembly.

21. The method according to claim 3, wherein the light for color measurement is white light.

22. The method according to claim 13, wherein the light for 3D measurement is blue light.

* * * * *